(12) United States Patent
Fukui et al.

(10) Patent No.: US 6,537,561 B1
(45) Date of Patent: Mar. 25, 2003

(54) FAT EMULSION FOR ORAL ADMINISTRATION

(75) Inventors: Hiroshi Fukui, Uji (JP); Junzo Seki, Ibaraki (JP)

(73) Assignee: Nippon Shinyaku Co., Ltd., Kyoto (JP)

( * ) Notice: Subject to any disclaimer, the term of this patent is extended or adjusted under 35 U.S.C. 154(b) by 0 days.

(21) Appl. No.: 09/367,650

(22) PCT Filed: Feb. 25, 1998

(86) PCT No.: PCT/JP98/00786

§ 371 (c)(1),
(2), (4) Date: Aug. 18, 1999

(87) PCT Pub. No.: WO98/37869

PCT Pub. Date: Sep. 3, 1998

(30) Foreign Application Priority Data

Feb. 27, 1997 (JP) .............................................. 9-043495

(51) Int. Cl.[7] .......................... A61K 9/127; A61K 9/107
(52) U.S. Cl. ...................... 424/400; 424/450; 424/455; 424/489; 424/502; 514/937; 514/938; 514/943
(58) Field of Search ................................ 424/400, 450, 424/489–502, 455; 514/937–943

(56) References Cited

U.S. PATENT DOCUMENTS

| 4,880,634 | A |   | 11/1989 | Speiser |
|---|---|---|---|---|
| 5,372,943 | A | * | 12/1994 | Inlow .................... 435/240.31 |
| 5,576,016 | A | * | 11/1996 | Amselem .................... 426/450 |
| 5,635,491 | A |   | 6/1997 | Seki et al. |
| 5,658,898 | A | * | 8/1997 | Weder ........................ 514/211 |
| 5,688,761 | A | * | 11/1997 | Owen ............................ 516/2 |
| 5,753,241 | A | * | 5/1998 | Ribien ........................ 424/401 |

FOREIGN PATENT DOCUMENTS

EP    0 315 079    5/1989

* cited by examiner

Primary Examiner—Gollamudi S. Kishore
(74) Attorney, Agent, or Firm—Eugene C. Rzucidlo

(57) ABSTRACT

An O/W medical fat emulsion for oral administration, which is capable of increasing the bioavailability of a medicine or the blood level thereof. The emulsion is composed of fat emulsion particles containing an oil component, an emulsifier and a medicine as the indispensable constituents and dispersed in water, characterized in that the average diameter of the particles in the fat emulsion ranges from 5 to 50 nm. A freeze-dried preparation of the emulsion is also included in the invention.

23 Claims, 1 Drawing Sheet

FAT EMULSION FOR ORAL ADMINISTRATION

TECHNICAL FIELD

The invention relates to a drug-containing o/w type fat emulsion for oral administration.

BACKGROUND ART

In order that the drug administered orally may be absorbed from the gastrointestinal tract, it is generally necessary that the drug be dissolved within the digestive tract in advance. Therefore, when the drug is a so-called lipophilic drug which is sparingly soluble in the digestive tract, improvements in its gastrointestinal absorption are generally sought by increasing its intra-gastrointestinal solubility through a variety of techniques such as salt formation, modification of crystal form, comminution, and use of a surfactant.

It may also be regarded as one of such pharmaceutical techniques to entrap a drug in fat emulsion particles and administer the resulting fat emulsion. Entrapping a drug in fat emulsion particles stabilizes the drug and improves its dispersibility in the digestive tract, with the result that increases in absorption area and solubility can be expected.

A fat emulsion comprising fat emulsion particles having an average particle diameter of not greater than 200 nm is also known (e.g. Tokkyo Kokai Koho H2-203) and it is generally considered that this emulsion can be administered orally and parenterally. There also is some literature describing pharmaceutical products for oral administration which are based on fat emulsions of relatively large particle size (e.g. Tokkyo Kokai Koho S61-56122).

However, it is suspected that when the conventional fat emulsion is administered orally, the emulsion particles of the fat emulsion are, destroyed by the enzymes in the digestive tract so that the components of the fat emulsion particle are absorbed independently of one another into the absorbing cells, with the result that even when a drug is administered orally in the form of a fat emulsion, the pharmacokinetics of the drug contained in the fat emulsion particles do not agree with the pharmacokinetics of the fat emulsion particles as such which apply to direct administration into the blood vessel. Therefore, when the conventional fat emulsion is administered orally, it seems difficult to achieve the expected effect in terms of absorption, avoidance of metabolism, and transfer to the target tissue.

In addition, the fat emulsion particles of the conventional fat emulsion are destroyed in the digestive tract, it seems difficult to find a correlation between the particle diameter of the particles constituting the fat emulsion and the bioavailability or blood concentration of the drug after oral administration or avoid recognition by the p-glycoprotein (discharging pump) in the absorbing cells of the digestive tract.

DISCLOSURE OF THE INVENTION

The invention has for its object to provide a medical o/w type fat emulsion for oral medication which insures a high bioavailability or blood concentration of a drug.

After intensive research the inventors of the invention found a medical o/w type fat emulsion capable of accomplishing the above object and have developed the invention.

The invention relates to an o/w fat emulsion in which fat emulsion particles composed essentially of an oil component, an emulsifier, and a drug are dispersed in water, characterized in that the average particle diameter of the fat emulsion particles is within the range of 5–50 nm, or a freeze-dried version of said emulsion. The invention further relates to an o/w fat emulsion for oral administration in which fat emulsion particles composed essentially of an oil component, a phospholipid, bile acid or a salt of bile acid, and a drug are dispersed in water, characterized in the average particle diameter of said fat emulsion particles lies within the range of 5–50 nm. By the use of a phospholipid and bile acid or a salt of bile acid in combination, the absorption of the drug from the gastrointestinal tract may be further enhanced.

The invention is now described in detail.

The oil component for use in the invention is not particularly restricted provided that it is an oil component which can be used in pharmaceutical products, thus including vegetable oil, animal oil, neutral lipid (mono-substituted, di-substituted or tri-substituted glyceride), synthetic oil or fat, and sterol derivatives. More particularly, the vegetable oil includes but is not limited to soybean oil, cottonseed oil, rapeseed oil, sesame oil, corn oil, peanut oil and safflower oil; the animal oil includes but is not limited to fish oil; the neutal lipid includes but is not limited to triolein, trilinolein, tripalmitin, tristearin, trimyristin and triarachidonin; the synthetic lipid includes but is not limited to azone; and the sterol derivatives include but are not limited to cholesteryl oleate, cholesteryl linoleate, cholesteryl myristate, cholesteryl palmitate and cholesteryl arachidate. Optionally, more than one of those substances may be employed in combination. The preferred oil component includes triglycerides and vegetable oils composed predominantly thereof. Soybean oil is preferred for practical purposes and, in particular, soybean oil purified to a high purity grade is preferred.

The oil component content of the fat emulsion for oral administration according to the invention (hereinafter referred to as "the emulsion of the invention") should vary according to species of the oil component used and other components but may judiciously be somewhere within the range of 0.1–30 w/v %, preferably 1–20 w/v %. The same range applies as well to the invention wherein bile acid or a salt of bile acid is one of the essential components of the fat emulsion particle.

The emulsifier for use in the invention is not particularly restricted provided that it can be used in pharmaceutical products, thus including phospholipids and nonionic surfactants. More particularly, the phospholipid includes but is not limited to phosphatidylcholine, phosphatidylethanolamine, phosphatidylinositol, phosphatidylserine, phosphatidylglycerol, sphingomyelin and lecithin. Hydrogenated phospholipids can also be used. The nonionic surfactant includes but is not limited to polyalkylene glycols (e.g. a polyethylene glycol with an average molecular weight of 1000–10000, preferably 4000–6000), polyoxyalkylene copolymers (e.g. a polyoxyethylene-polyoxypropylene copolymer with an average molecular weight of 1000–20000, preferably 6000–10000), hydrogenated castor oil-polyoxyalkylene derivatives (e.g. hydrogenated castor oil-polyoxyethylene(20)-ether, (40)-ether, and (100)-ether), and castor oil-polyoxyalkylene derivatives (e.g. castor oil-polyoxyethylene (20)-ether, (40)-ether, and (100)-ether). Those may be used in a combination of two or more different species. As the preferred emulsifier, egg yolk phosphatidylcholine, egg yolk lecithin and soybean lecithin can be mentioned. For practical purposes, egg yolk lecithin and soybean lecithin are preferred. As the phospholipid for use in the invention wherein bile acid or a salt of bile acid is used as an essential component, too, egg yolk phosphatidylcholine, egg yolk lecithin and soybean lecithin are preferred.

The emulsifier content of the emulsion of the invention varies with different species of the emulsifier and other components but may judiciously be somewhere within the range of 0.05–40 w/v %, preferably 0.1–20 w/v %. The same range applies as well to the phospholipid for use in the invention wherein bile acid or a salt of bile acid is used as one of the essential components.

The bile acid or the salt of bile acid, which can be used in the invention, includes but is not limited to taurocholic acid, sodium taurocholate, glycocholic acid, sodium glycocholate, sodium taurodeoxycholate, deoxycholic acid and sodium deoxycholate. Those compounds can be used in a combination of two or more species. As the preferred bile acid or salt of bile acid, taurocholic acid and sodium taurocholate can be mentioned. Particularly when the phospholipid is lecithin, the concomitant use of sodium taurocholate as said bile acid or salt of bile acid is preferred.

The bile acid or bile acid salt content of the emulsion of the invention should vary with different species of bile acid or equivalent used and other components but may judiciously be somewhere within the range of 0.05–40 w/v %, preferably 0.1–20 w/v %.

The weight ratio of the oil component to the emulsifier (oil/emulsifier) can be judiciously selected from the range of 0.1–20, preferably 0.4–6.0, more preferably 0.8–1.2 (1 in particular). The weight ratio of the oil component to the phospholipid and the bile acid or salt of bile acid (oil/phospholipid plus bile acid or salt of bile acid) may be judiciously selected from the range of 0.1–20, preferably 0.4–6.0, more preferably 0.8–1.2 (1 in particular).

The drug for use in the invention is, not particularly restricted but is preferably a drug which is generally referred to as a lipophilic drug. Moreover, since the emulsion of the invention is not destroyed by gastrointestinal enzymes but is absorbed in a substantially intact vesicular form, it is particularly useful for the delivery of drugs recognized by p-glycoprotein. Among such drugs are cyclosporin, adriamycin, vincristine and bleomycin. The P-glycoprotein exists on the cell membrane of cerebral vascular endothelial cells and gastrointestinal tract cells and is known to be a protein having a pumping action which recognizes any foreign matter entering the cell and pumps it out from the cell [e.g. Yuzuru Tatsuta et al., Protein, Nucleic Acid and Enzyme, 38, 1501–1509 (1993)].

The drug content of the emulsion of the invention should vary with different kinds of drugs and other components but may judiciously be selected from the range of 0.05–20 w/v %.

Furthermore, in the practice of the invention, an auxiliary emulsifier/emulsion stabilizer can be added. As examples of such auxiliary emulsifier/emulsion stabilizer, there can be mentioned straight-chain or branched-chain saturated or unsaturated fatty acids of 6–22 carbon atoms, specifically stearic acid, oleic acid, linoleic acid, palmitic acid, linolenic acid, myristic acid and their salts [e.g. alkali metal salts (sodium salt, potassium salt, etc.), alkaline earth metal salts (calcium salt etc.), etc.], aliphatic primary amines or aliphatic secondary amines containing 2–22 carbon atoms, specifically ethanolamine, propylamine, octylamine, stearylamine, oleylamine, etc., basic amino acids such as lysine, histidine, ornithine, arginine, etc., sterols such as cholesterol, cholestanol, etc., phosphatidic acids and charged substances such as gangliosides and stearylamine.

Those substances can be used not only singly or in a suitable combination of more than one species.

The amount of such supplemental components in the emulsion of the invention should vary with intended uses of the emulsion and other factors but the recommended amount is generally not greater than 2 w/v %, preferably not greater than 1 w/v %.

In addition, various additives such as antioxidant, preservative, isotonizing agent, buffer, stabilizer, etc., auxiliary substances and nutrients may also be optionally added. Specifically, benzoic acid, ascorbic acid, tocopherol, etc. can be mentioned by way of example. Those substances can be generally incorporated in suitable amounts and the level of addition below 10 w/v % is sufficient.

The average particle diameter of the fat emulsion particles of the invention is 5–50 nm, preferably 5–40 nm, more preferably 10–30 nm.

While the fat emulsion particles of the invention exist as dispersed in water, the water may for example be tap water, purified water, distilled water or water for injection.

The emulsion of the invention can be lyophilized to provide a freeze-dried preparation. However, since the emulsion of the invention, which is intended for medical use, should be such that when redissolved in water or dissolved in the digestive tract, the freeze-dried preparation may reconstitute itself into a substantially original emulsion, it is preferable to formulate an excipient for that purpose (a lyophilization auxiliary agent). The excipient mentioned above includes but is not limited to saccharides. Preferred are disaccharides, and as specific examples, maltose, trehalose, and sucrose can be mentioned. In particular, maltose is preferred.

The amount of said excipient in the emulsion of the invention should vary with different species of the; excipient and other components but may judiciously be selected from the range of 1–30 w/v %, more preferably 3–20 w/v %.

The emulsion of the invention can be produced by the conventional technology. An exemplary production process comprises adding the drug, said emulsifier, optionally as well as bile acid and/or a salt of bile acid and other additives in suitable amounts to a predetermined amount of the oil component, homogenizing the mixture with or without heating, adding a suitable amount of water, and emulsifying the whole mixture with a homogenizing machine such as the conventional homo-mixer, homogenizer, ultrasonic homogenizer, Microfluidizer (brand name), Nanomizer (brand name), Ultimizer (brand name) or Manton-Gaulin pressure homogenizer.

The freeze-dried version of the emulsion of the invention can be manufactured by lyophilizing the emulsion of the invention by the conventional technology. An exemplary process comprises sterilizing the emulsion of the invention, dispensing the emulsion in predetermined amounts into vials, performing preliminary lyophilization at about −40–−20° C. for about 2 hours, then performing primary drying under reduced pressure at about 0–10° C. and finally performing secondary drying under reduced pressure at about 15–25° C. This sequence is generally followed by purging the internal air of the vials with nitrogen gas and stoppering the vials to provide the objective freeze-dried version of the emulsion of the invention.

The freeze-dried preparation of the invention can be directly administered without redissolving it in advance. Optionally, it can be first reconstituted by adding a suitable solution (a reconstitution medium) with or without the aid of stirring for redissolution and, then, administered. The reconstitution medium includes but is not limited to tap water, purified water, distilled water, water for injection, physiological saline, general infusions and drinking water. The proportion of the reconstitution medium is not particularly restricted but may judiciously be 0.5–2 times the volume of the emulsion prior to lyophilization or not greater than 500 ml.

The freeze-dried preparation according to the invention can be pulverized and, optionally after addition of a suitable excipient, be processed into fine granules, powders, capsules and liquids (inclusive of syrups) or compression-molded together with a suitable excipient to provide tablets. Those tablets can be coated with a suitable coating agent.

The emulsion of the invention or the freeze-dried version thereof can be administered, whether as it is or after redissolution and/or suitable processing, orally to animals inclusive of humans.

BEST MODE FOR CARRYING OUT THE INVENTION

The following examples and test examples illustrate the invention in further detail.

EXAMPLE 1

To 500 mg of soybean oil were added 500 mg of egg yolk lecithin and 8 mg of nifedipine (a calcium channel blocker) followed by addition of 10 ml of physiological saline. Using a probe type ultrasonic homogenizer (Branson Sonifier Model 185, the same applies hereinafter), the mixture was sonicated under iced water-cooling for 60 minutes. The nifedipine-containing fat emulsion thus obtained was yellow and transparent. Moreover, the weight average particle diameter of the fat emulsion particles as determined with a light-scattering particle size analyzer (Otsuka Denshi, DLS-7000; the same applies hereinafter) was 20.1 nm. It was also confirmed by transmission electron microscopy that those fat emulsion particles were uniform and spherical ultrafine particles and did not contain a lipid bilayer or lamellar structure such as that of liposomes. In addition, this fat emulsion passed 100% through a 0.2 μm membrane filter, indicating that it did not contain fat emulsion particles in excess of 0.2 μm in diameter.

EXAMPLE 2

To 300 mg of cholesteryl oleate were added 500 mg of soybean lecithin and 8 mg of nifedipine followed by addition of 10 ml of 0.24 M glycerin/water. Using the probe type ultrasonic homogenizer, the mixture was sonicated under iced water-cooling for 40 minutes. The nifedipine-containing fat emulsion thus obtained was yellow and transparent and the average particle diameter of the fat emulsion particles as determined with a light-scattering particle size analyzer was 39.7 nm. It was also confirmed by transmission electron microscopy that those fat emulsion particles were uniform and spherical ultrafine particles and did not contain a lipid bilayer structure such as that of liposomes. In addition, this fat emulsion passed 100% through a 0.2 μm membrane filter, indicating that it did not contain fat emulsion particles in excess of 0.2 μm in diameter.

EXAMPLE 3

To 27 mg of triolein were added 40 mg of egg yolk lecithin and 10 mg of guaiazulene (an antiinflammatory drug) followed by addition of 10 ml of 0.24 M glycerin/water. Using the probe type ultrasonic homogenizer, the mixture was sonicated under iced water-cooling for 60 minutes. The guaiazulene-containing fat emulsion thus obtained was blue and transparent and the average particle diameter of the fat emulsion particles as determined with a light-scattering particle size analyzer was 23.1 nm. It was also confirmed by transmission electron microscopy that those fat emulsion particles were uniform and spherical ultrafine particles and did not contain a lipid bilayer structure such as that of liposomes. In addition, this fat emulsion passed 100% through a 0.2 μm membrane filter, indicating that it did not contain fat emulsion particles in excess of 0.2 μm in diameter.

EXAMPLE 4

To 500 mg of soybean oil were added 500 mg of egg yolk lecithin, 200 mg of sodium taurocholate and 8 mg of nifedipine followed by addition of 10 ml of physiological saline. Using the probe type ultrasonic homogenizer, the mixture was sonicated under iced water-cooling for 60 minutes. The nifedipine-containing fat emulsion thus obtained was yellow and transparent and the average particle size of the fat emulsion particles as determined with a light-scattering particle size analyzer was 19.7 nm. It was also confirmed by transmission electron microscopy that those fat emulsion particles were uniform and spherical ultrafine particles and did not contain a lipid bilayer structure such as that of liposomes. In addition, this fat emulsion passed 100% through a 0.2 μm membrane filter, indicating that it did not contain fat emulsion particles in excess of 0.2 μm in diameter.

Test Example 1

Pharmacokinetics (1)

To 500 mg of soybean oil were added 500 mg of egg yolk lecithin, 10 kBq (3 pg) of $^3$H-cholesteryl hexadecyl ether, 5 kBq (2.4 μg) of $^{14}$C-nifedipine and 8 mg of unlabeled nifedipine, and the mixture was dissolved in chloroform. The chloroform was then evaporated under reduced pressure. To the residue was added 10 ml of 0.24 M glycerin/water, and using the probe type ultrasonic homogenizer, the mixture was sonicated under iced water-cooling for 5 min., 10 min., 20 min., 40 min., 60 min. or 90 min. The resulting fat emulsion was yellow and transparent. The average particle diameter of fat emulsion particles as determined with a light-scattering particle size analyzer at each point of time is shown in Table 1.

TABLE 1

| Average particle diameter of fat emulsion particles | | | | | | |
|---|---|---|---|---|---|---|
| Treating time (min.) | 5 | 10 | 20 | 40 | 60 | 90 |
| Average particle dia. (nm) | 255 | 141 | 88 | 56 | 32 | 21 |

The fat emulsion at each point of time was administered orally to 7-week-old male SD rats (body weights ca 240 g) in a dose volume of 5 ml/kg and the plasma radioactivity level was serially determined. The radioactivity was derived from the two labels used, i.e. the $^{14}$C label reflecting the pharmacokinetics of the drug nifedine and the $^3$H-label reflecting the pharmacokinetics of the core of the fat emulsion particle. By determining both $^{14}$C and $^3$H in parallel, the pharmacokinetics of the drug and the fat emulsion particle were compared. The results are presented in FIG. 1.

It will be apparent from FIG. 1 that among the fat emulsions with average particle diameters of 255 nm–56 nm, there was little difference in the area under the plasma concentration-time curve (AUC). On the other hand, when those fat emulsions were compared with the fat emulsions having average particle diameters of 32 nm and 21 nm, a considerable difference was found in AUC and it was also found that the individual variation was smaller for the fat emulsions having average particle diameters of 32 nm and 21 nm. Moreover, the fat emulsions from 255 nm to 56 nm in average particle diameter gave AUC values not much different from the AUC value found when a solubilized preparation (nifedipine 5 mg, polyethylene glycol 400 (PEG400) 2 ml, ethanol 4 ml, and saline the balance to make 10 ml) was administered orally in the same nifedipine dose. In the comparison of the AUC values of the emulsions from 255 nm to 56 nm in average particle diameter with the AUC values of the emulsions having average particle diameters of 32 nm and 21 nm, a significant difference was invariably found at $p<0.05$.

Furthermore, whereas the time course of plasma $^{14}C$ concentration was substantially the same as the time course of plasma $^{3}H$ concentration for the fat emulsions not larger than 50 nm, no agreement was found for the fat emulsions larger than 50 nm. Thus, with the fat emulsions over 50 nm, the drug and the fat emulsion particle showed dissimilar pharmacokinetics, while the fat emulsions not over 50 nm showed comparable pharmacokinetics.

Test Example 2

Pharmacokinetics (2)

To 500 mg of soybean oil were added 500 mg of egg yolk lecithin, 10 kBq (3 pg) of $^{3}H$-dipalmitoylphosphatidylcholine, 5 kBq (2.4 μg) of $^{14}C$-nifedipine and 8 mg of unlabeled nifedipine, and the mixture was dissolved in chloroform. The chloroform was then evaporated under reduced pressure. To the residue was added 10 ml of 0.24 M glycerin/water, and using the probe type ultrasonic homogenizer, the mixture was sonicated under iced water-cooling for 5 min., 10 min., 20 min., 40 min., 60 min. or 90 min. The resulting fat emulsion was yellow and transparent. The average particle diameter of fat emulsion particles as determined with a light-scattering particle size analyzer at each point of time is shown in Table 2.

TABLE 2

Average particle diameter of fat emulsion particles

| Treating time (min.) | 5 | 10 | 20 | 40 | 60 | 90 |
|---|---|---|---|---|---|---|
| Average particle dia. (nm) | 275 | 160 | 79 | 55 | 41 | 28 |

As in Test Example 1, the fat emulsion at each point of time was administered orally to rats in a dose volume of 5 ml/kg and the plasma radioactivity level was determined. The radioactivity derived from the $^{14}C$ label reflecting the pharmacokinetics of the drug nifedipine and that from the 3H label reflecting the pharmacokinetics of the surface layer of the fat emulsion particle were concurrently measured. The results are presented in FIG. 2.

It will be apparent from FIG. 2 that, just as in Test Example 1, there was little variation in AUC within the average particle diameter range of 275 nm–55 nm. In contrast, a considerable difference was found in AUC between those fat emulsions on one hand and the fat emulsions having average particle diameters of 41 nm and 28 nm on the other hand, and the individual variation was also smaller for the fat emulsions having average particle diameters of 41 nm and 28 nm. Furthermore, the fat emulsions from 275 nm to 55 nm in average particle diameter gave AUC values not much different from the AUC value found when a solubilized preparation (nifedipine 5 mg, polyethylene glycol 400 (PEG 400) 2 ml, ethanol 4 ml and saline the balance to make 10 ml) was administered orally in the same nifedipine dose. When the AUC values of 275 nm–55 nm emulsions were compared with the AUC values of 41 nm and 28 nm emulsions, a significant difference at $p<0.05$ was invariably found.

Furthermore, whereas the time course of plasma $^{14}C$ concentration was substantially the same as the time course of plasma $^{3}H$ concentration for the fat emulsions not larger than 50 nm, no agreement was found for the fat emulsions larger than 50 nm. Thus, with the fat emulsions over 50 nm, the drug and the fat emulsion particle showed dissimilar pharmacokinetics, although the fat emulsions not larger than 50 nm showed comparable pharmacokinetics.

Test Example 3

To 1 g of soybean oil were added 1 g of egg yolk lecithin and 20 mg of Oil Red XO(OR) followed by addition of 20 ml of 0.24 M glycerin/water. Using the probe type ultrasonic homogenizer, the mixture was sonicated under iced water-cooling for 90 minutes. The average particle diameter of the resulting OR-containing fat emulsion particles was 31 nm. Then, to 2 g of soybean oil were added 240 mg of egg yolk lecithin and 20 mg of Oil Red XO(OR), followed by addition of 20 ml of 5% glucose/water. Using the probe type ultrasonic homogenizer, the mixture was sonicated under iced water-cooling for 30 minutes. The average particle diameter of the resulting OR-containing fat emulsion particles was 308 nm.

The above two kinds of OR-containing fat emulsions were respectively administered orally to 7-week-old male SD rats (body weights ca 240 g) inserted a cannula into the thoracic duct vasa lymphatica for comparing the amounts of transfer to the lymph. The amount of transfer to the lymph up to 1 hour after oral administration was 20-fold larger for the fat emulsion having an average particle diameter of 31 nm as compared with the 308 nm fat emulsion.

Test Example 4

Using the same OR-containing fat emulsions as used in Test Example 3 and an aqueous suspension of OR, membrane permeation experiments were performed in cultured cells. Thus, using the Caco-2 monolayer cultured on Transwell (at day 15–20 of culture), the permeation amount of OR was measured under the conditions of pH 7.4, 37° C. and 90 minutes. As a result, the fat emulsion having an average particle diameter of 31 nm showed a permeation amount about 3-fold larger as compared with the 308 nm emulsion and about 4-fold larger as compared with the aqueous suspension.

Test Example 5

The fat emulsions according to Example 1 and Example 4 were respectively administered orally to 7-week-old male SD rats (body weights ca 240 g) and the plasma nifedipine concentrations were determined. As a result, compared with the fat emulsion of Example 1, the fat emulsion of Example 4 gave an AUC value about 3-fold as high.

Test Example 6

To 700 mg of soybean oil were added 800 mg of egg yolk lecithin and150 mg of cyclosporin A (an immunosuppressant) followed by addition of 10 ml of saline. Using the probe type ultrasonic homogenizer, the mixture was sonicated under iced water-cooling for 30 minutes or 60 minutes. The average particle diameter of the resulting cyclosporin A-containing fat emulsion particles was 62 nm for the 30-minute sonication product versus 35 nm for the 60-minute sonication product.

The above two kinds of fat emulsions were respectively administered orally to male beagle dogs (body weights ca 10.5 kg) in a cyslosporin dose of 50 mg and the blood cyclosporin A concentrations were determined. As a result, the emulsion of the invention (60-minute sonication product, average particle diameter 35 nm) gave an AUC value approximately 4-fold larger than the emulsion having an average particle diameter of 62 nm. The individual variation was smaller for the emulsion of the invention than for the fat emulsion having an average particle diameter of 62 nm.

Test Example 7

Cyclosporin A-containing fat emulsions similar to those used in Test Example 6 were prepared using $^3$H-cyclosporin A and membrane permeation experiments were similarly performed in cultured cells. Thus, using a Caco-2 monolayer as in Test Example 4, $^3$H-cyclosporin A was added at a concentration of 0.2 $\mu$M and the amount of permeation during 60 minutes was determined. As a result, the fat emulsion having an average particle diameter of 35 nm gave a permeation amount about 2-fold larger than the 62 nm fat emulsion.

In addition, when the cultured cells were treated with 100 $\mu$M verapamil (a calcium channel blocker) or 100 $\mu$M adriamycin (an antineoplastic drug) for 30 minutes in advance in otherwise the same experimental system, the permeation amount for the 35 nm fat emulsion was not different from the amount found without the pretreatment but the 62 nm fat emulsion showed an increased permeation amount. It was, therefore, found that whereas the drug in the fat emulsion having an average particle diameter of 62 nm was recognized by P-glycoprotein, the drug in the emulsion of the invention evaded the recognition by P-glycoprotein.

EFFECTS OF THE INVENTION

The following list can be given as the effects of the invention.
(1) With the emulsion of the invention, the bioavailability or blood concentration of a drug and the absorption of the drug from the digestive tract following oral administration can be remarkably increased as compared with the conventional fat emulsion.
(2) The fat emulsion particles constituting the emulsion of the invention are hardly susceptible to enzymatic, chemical or physical attacks in the digestive tract but are absorbed retaining their original form without collapsing so that the drug administered is protected against metabolism in the digestive tract and, after absorption, the intrinsic characteristics of the fat emulsion particles such as avoidance of metabolism and good transfer to the target tissue can be fully exploited.
(3) The drug incorporated in the emulsion of the invention evades the recognition by P-glycoprotein and, therefore, is useful for the delivery of drugs which are otherwise recognized by P-glycoprotein.
(4) With the emulsion of the invention which contains bile acid or a salt of bile acid, still improved absorption from the digestive tract can be insured for certain kinds of drugs.

Figure 1:
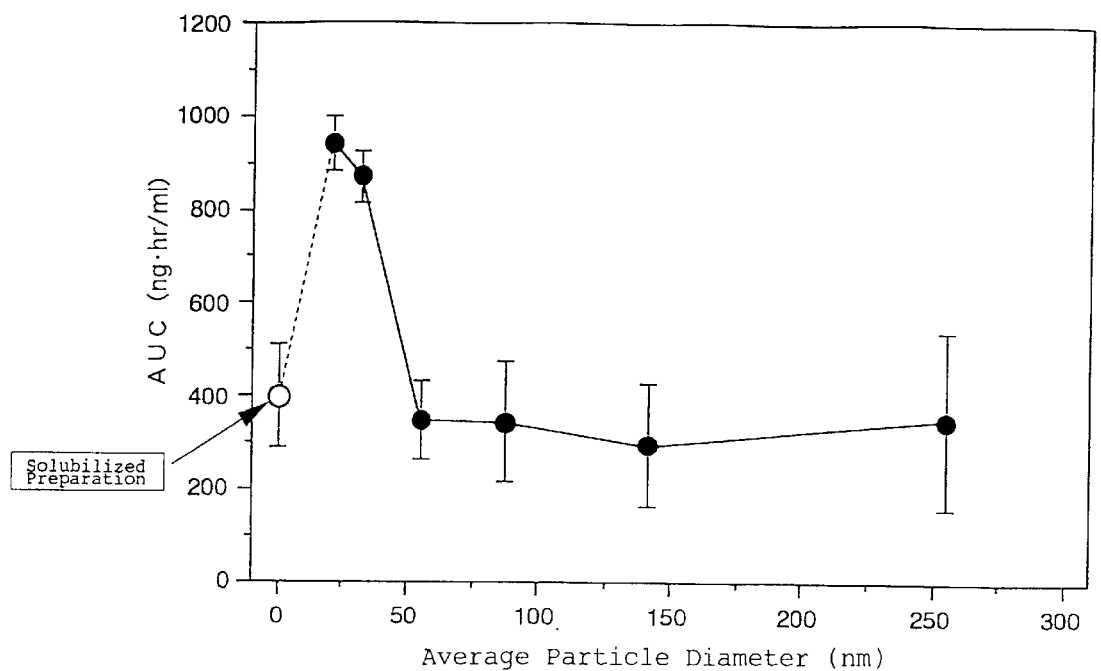
FIG. 1 shows the relationship of the average particle diameter of fat emulsion particles to the area under the plasma concentration-time curve (AUC). The AUC (ng·hr/ml) is plotted on the ordinate and the average particle diameter (nm) of fat emulsion particles on the abscissa. The closed circle represents data on nifedipine-containing fat emulsions and the open circle represents data on a nifedipine-containing solubilized preparation.
Figure 2:
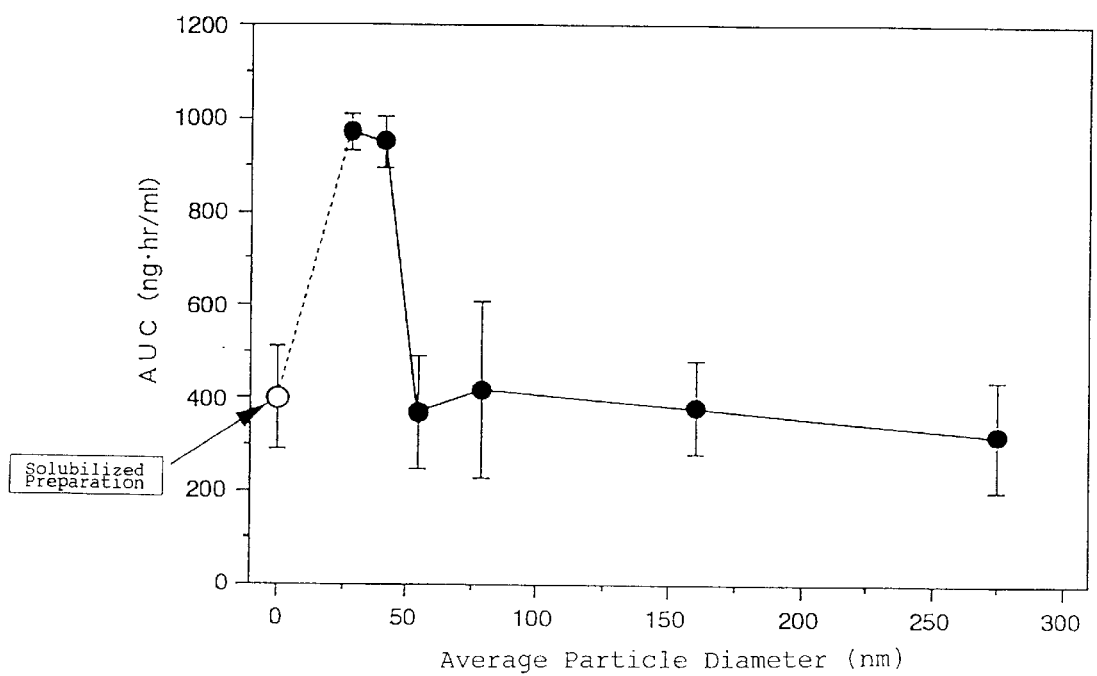
FIG. 2 shows the relationship of the average particle diameter of fat emulsion particles to the area under the plasma concentration-time curve (AUC). The AUC (ng·hr/ml) is plotted on the ordinate and the average particle diameter (nm) of fat emulsion particles on the abscissa. The closed circle represents data on nifedipine-containing fat emulsions and the open circle represents data on a nifedipine-containing solubilized preparation.

What is claimed is:

1. An o/w fat emulsion, or a freeze-dried version thereof, for oral administration to an individual comprising an aqueous dispersion of uniform and spherical ultrafine fat emulsion particles, each of which is composed essentially of a vegetable oil, a phospholipid or nonionic surfactant as an emulsifier and a drug suitable for inclusion in said emulsion particles, wherein the average particle diameter of said fat emulsion particles is from about 20 nm to about 41 nm and wherein said emulsion is such that, upon oral administration to an individual, absorption of said drug into the bloodstream of said individual is enhanced.

2. The fat emulsion for oral administration or freeze-dried version according to claim 1 wherein the drug is one which is by nature recognized by p-glycoprotein in the absorbing cells of the digestive tract.

3. The fat emulsion for oral administration or freeze-dried version according to claim 1 wherein the vegetable oil content lies within the range of 0.1–30 w/v % and the emulsifier content lies within the range of 0.05–40 w/v %.

4. The fat emulsion for oral administration or freeze-dried version according to claim 1 wherein the weight ratio of the vegetable oil to the emulsifier (oil/emulsifier) lies within the range of 0.1–20.

5. The fat emulsion for oral administration or freeze-dried version according to claim 4 wherein the vegetable oil is soybean oil and the phospholipid is egg yolk lecithin.

6. The fat emulsion for oral administration or freeze-dried version according to claim 1 further comprising a saccharide.

7. The fat emulsion for oral administration or freeze-dried version according to claim 6 wherein the saccharide content is 1–30 w/v %.

8. The fat emulsion for oral administration or freeze-dried version according to claim 6 wherein the saccharide is a disaccharide.

9. The fat emulsion for oral administration or freeze-dried version according to claim 1 further comprising a fatty acid and/or cholesterol.

10. An o/w fat emulsion, or a freeze-dried version thereof, for oral administration to an individual comprising an aqueous dispersion of uniform and spherical ultrafine fat emulsion particles, each of which is composed essentially of a vegetable oil, a phospholipid, and bile acid or a salt of a bile acid as an emulsifier, and a drug suitable for inclusion in said emulsion particles, wherein the average particle diameter of the fat emulsion particles is and wherein said emulsion is such that, upon oral from about 20 nm to about 41 nm, absorption of said drug into the bloodstream of said individual is enhanced.

11. The fat emulsion for oral administration or freeze-dried version according to claim 10 wherein the drug is one which is by nature recognized by p-glycoprotein in the digestive tract.

12. The fat emulsion for oral administration or freeze-dried version according to claim 10 wherein the vegetable oil content lies within the range of 0.1–30 w/v %, the phospholipid content lies within the range of 0.05–40 w/v %, and the bile acid or bile acid salt content lies within the range of 0.05–40 w/v %.

13. The fat emulsion for oral administration or freeze-dried version according to claim 10 wherein the weight ratio of the vegetable oil to the phospholipid and bile acid or bile acid salt (oil/(phospholipid+bile acid or bile acid salt)) lies within the range of 0.1–20.

14. The fat emulsion for oral administration or freeze-dried version according to claim 10 wherein the phospholipid is lecithin, and the bile acid or salt of bile acid is a salt of taurocholic acid.

15. The fat emulsion for oral administration or freeze-dried version according to claim 14 wherein the vegetable oil is soybean oil, the lecithin is egg yolk lecithin, and the bile acid or salt of bile acid is sodium taurocholate.

16. The fat emulsion for oral administration or freeze-dried version according to claim 10 further comprising a saccharide.

17. The fat emulsion for oral administration or freeze-dried version according to claim 16 wherein the saccharide content is 1–30 w/v %.

18. The fat emulsion for oral administration or freeze-dried version according to claim 16 wherein the saccharide is a disaccharide.

19. The fat emulsion for oral administration or freeze-dried version according to claim 10 further comprising a fatty acid and/or cholesterol.

20. A method of preventing the destruction of fat emulsion particles in the digestive tract of an individual and enhancing the absorption of a drug included in such emulsion particles into the bloodstream from the digestive tract of such individual which comprises orally administering to an individual in need thereof an effective amount of an o/w fat emulsion which comprises an aqueous dispersion of uniform and spherical ultrafine fat emulsion particles, each of which is composed essentially of a vegetable oil, a phospholipid or nonionic surfactant as an emulsifier and a drug suitable for inclusion in said emulsion particles, wherein the average particle diameter of the fat emulsion particles is from about 20 nm to about 41 nm.

21. A method according to claim 20 wherein each fat emulsion particle contains a bile acid or a salt thereof as the emulsifier.

22. A method of avoiding recognition of a drug by p-glycoprotein in the absorbing cells of the digestive tract of an individual which comprises orally administering to an individual in need thereof an effective amount of an o/w fat emulsion which comprises an aqueous dispersion of uniform and spherical ultrafine fat emulsion particles, each of which is composed essentially of a vegetable oil, a phospholipid or nonionic surfactant as an emulsifier and a drug suitable for inclusion in said emulsion particles, wherein the average particle diameter of the fat emulsion particles is from about 20 nm to about 41 nm.

23. A method according claim 22 wherein each fat emulsion particle contains a bile acid or a salt thereof as the emulsifier.

* * * * *